US010240206B2

(12) United States Patent
Cress et al.

(10) Patent No.: US 10,240,206 B2
(45) Date of Patent: Mar. 26, 2019

(54) BIOMARKERS AND METHODS FOR PREDICTING BENEFIT OF ADJUVANT CHEMOTHERAPY

(71) Applicant: H. Lee Moffitt Cancer Center and Research Institute, Inc., Tampa, FL (US)

(72) Inventors: W. Douglas Cress, Lutz, FL (US); Dung-Tsa Chen, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 0 days.

(21) Appl. No.: 14/765,156

(22) PCT Filed: Feb. 3, 2014

(86) PCT No.: PCT/US2014/014378
§ 371 (c)(1),
(2) Date: Jul. 31, 2015

(87) PCT Pub. No.: WO2014/121177
PCT Pub. Date: Aug. 7, 2014

(65) Prior Publication Data
US 2015/0376713 A1 Dec. 31, 2015

Related U.S. Application Data

(60) Provisional application No. 61/759,763, filed on Feb. 1, 2013.

(51) Int. Cl.
*C12Q 1/6886* (2018.01)
*G01N 33/574* (2006.01)
*A61N 5/10* (2006.01)
*G06F 19/22* (2011.01)

(52) U.S. Cl.
CPC ............ *C12Q 1/6886* (2013.01); *A61N 5/10* (2013.01); *C12Q 2600/106* (2013.01); *C12Q 2600/158* (2013.01); *C12Q 2600/16* (2013.01); *G06F 19/22* (2013.01)

(58) Field of Classification Search
None
See application file for complete search history.

(56) References Cited

U.S. PATENT DOCUMENTS

| 8,415,102 | B2 | 4/2013 | Geiss et al. | |
|---|---|---|---|---|
| 2010/0015607 | A1 | 1/2010 | Geiss et al. | |
| 2010/0047924 | A1 | 2/2010 | Webster et al. | |
| 2010/0112710 | A1 | 5/2010 | Geiss et al. | |
| 2010/0261026 | A1 | 10/2010 | Ferree et al. | |
| 2011/0129833 | A1* | 6/2011 | Baker | C12Q 1/6886 435/6.11 |
| 2012/0028907 | A1 | 2/2012 | Shakney | |
| 2014/0045915 | A1* | 2/2014 | Skog | C12Q 1/6806 514/44 A |

FOREIGN PATENT DOCUMENTS

| WO | 2007/076129 A2 | 7/2007 |
|---|---|---|
| WO | 2007/076132 A2 | 7/2007 |
| WO | 2008/124847 A2 | 10/2008 |
| WO | 2010/019826 A1 | 2/2010 |
| WO | 2012040784 A1 | 4/2012 |

OTHER PUBLICATIONS

Chen et al. Prognostic and Predictive Value of a Malignancy-Risk Gene Signature in Early-Stage Non-Small Cell Lung Cancer—Supplementary Table 1. 2011. J Natl Cancer Inst. vol. 103, No. 24, 32 pages.*
Chen et al. Early2 factor (E2F) deregulation is a prognostic and predictive biomarker in lung adenocarcinoma. 2016. Oncotarget, vol. 7, No. 50, pp. 82254-82265.*
Aberle, D.R., et al., Reduced lung-cancer mortality with low-dose computed tomographic screening. The New England journal of medicine, 2011. 365(5): p. 395-409.
Ma, Y., et al., A small-molecule E2F inhibitor blocks growth in a melanoma culture model. Cancer Res, 2008. 68(15): p. 6292-9.
Sage, J., Hope in sight for retinoblastoma. Nat Med, 2007. 13(1): p. 30-1.
La Thangue, N.B., the yin and yang of E2F-1: balancing life and death. Nat Cell Biol, 2003. 5(7): p. 587-9.
Johnson, D.G. and J. Degregori, Putting the Oncogenic and Tumor Suppressive Activities of E2F into Context. Curr Mol Med, 2006. 6(7): p. 731-8.
Chen, D.T., et al., Prognostic and predictive value of a malignancy-risk gene signature in early-stage non-small cell lung cancer. J Natl Cancer Inst, 2011. 103(24): p. 1859-1870.
Gazdar, A.F. and J.H. Schiller, Predictive and prognostic factors for non-small cell lung cancer—potholes in the road to the promised land. Journal of the National Cancer Institute, 2011. 103(24): p. 1810-1.
Kratz, J.R., et al., a practical molecular assay to predict survival in resected non-squamous, non-small-cell lung cancer: development and international validation studies. Lancet, 2012, 379(9818): p. 823-832.
Xie, Y., et al., Robust Gene Expression Signature from Formalin-Fixed Paraffin-Embedded Samples Predicts Prognosis of Non-Small-Cell Lung Cancer Patients. Clin Cancer Res, 2011, 1: 17(17): 5705-14.
Strauss, G.M., et al., Adjuvant paclitaxel plus carboplatin compared with observation in stage IB non-small-cell lung cancer: CALGB 9633 with the Cancer and Leukemia Group B, Radiation Therapy Oncology Group, and North Central Cancer Treatment Group Study Groups. J Clin Oncol, 2008. 26(31): p. 5043-51.
Northcott, P.A. et al, "Rapid, reliable, and reproducible molecular sub-grouping of clinical medulloblastoma samples", Acta Neuropathol, 2012, 123(4):615-26.

(Continued)

*Primary Examiner* — Channing S Mahatan
(74) *Attorney, Agent, or Firm* — Meunier Carlin & Curfman LLC

(57) ABSTRACT

Biomarkers, methods, assays, and kits are provided for predicting the efficacy of adjuvant chemotherapy (ACT) in a subject with early-stage non-small cell lung cancer (NSCLC).

4 Claims, 2 Drawing Sheets

(56) References Cited

OTHER PUBLICATIONS

Zhu, et al., "Prognostic and Predictive Gene Signature for Adjuvant Chemotherapy in Resected Non-Small-Cell Lung Cancer" Journal of Clinical Oncology, 2010 28:4417-4424.

Douillard, et al., "Adjuvant vinorelbine plus cisplatin versus observation in patients with completely resected stage IB-IIIA non-small-cell lung cancer (Adjuvant Navelbine International Trialist Association [ANITA]): a randomised controlled trial", Lancet Oncology 2006, vol. 7, No. 9:719-727.

Tang, et al., "A 12-Gene Set Predicts Survival Benefits from Adjuvant Chemotherapy in Non-Small Cell Lung Cancer Patients", Clinical Cancer Research 2013, 19:1577-86.

Wistuba, et al., "Validation of a Proliferation-Based Expression Signature as Prognostic Marker in Early Stage Lung Adenocarcinoma", Clinical Cancer Research 2013, 19:6261-71.

Felip, et al., "Preoperative Chemotherapy Plus Surgery Versus Surgery Plus Adjuvant Chemotherapy Versus Surgery Alone in Early-Stage Non-Small-Cell Lung Cancer", Journal Clin Oncol 2010, vol. 28, No. 19:3138-3145.

International Search Report, dated Mar. 21, 2014, in International Application No. PCT/US14/14378, 7 pages.

Geiss, G.K., et al., Direct multiplexed measurement of gene expression with color-coded probe pairs. Nat Biotechnol, 2008. 26(3): p. 317-25.

Malkov, V.A., et al., Multiplexed measurements of gene signatures in different analytes using the Nanostring nCounter Assay System. BMC Res Notes, 2009. 2: p. 80, 9 pages.

Reis, P.P., et al., mRNA transcript quantification in archival samples using multiplexed, color-coded probes. BMC Biotechnol, 2011. 11: p. 46, 10 pages.

\* cited by examiner

BIOMARKERS AND METHODS FOR PREDICTING BENEFIT OF ADJUVANT CHEMOTHERAPY

CROSS-REFERENCE TO RELATED APPLICATIONS

This application claims benefit of U.S. Provisional Application No. 61/759,763, filed Feb. 1, 2013, which is hereby incorporated herein by reference in its entirety.

STATEMENT REGARDING FEDERALLY SPONSORED RESEARCH OR DEVELOPMENT

This invention was made with Government Support under Agreement CA119997, CA129343, CA163068, and CA118809 awarded by the National Institutes of Health. The Government has certain rights in the invention.

BACKGROUND

Lung cancer accounts for over 160,000 deaths per year in the U.S., more than breast, colon, prostate and pancreatic cancer combined. The overall five-year survival rate for lung cancer is approximately 15%, and unlike other solid tumors, such as colon or breast cancer, little progress has been made in improving survival. Early-stage non-small cell lung cancer (NSCLC) is primarily treated by surgical resection. Unfortunately, after resection, one-third to one-half of early-stage patients will die of metastatic recurrence. Adjuvant chemotherapy (ACT) improves the survival of patients with early-stage disease and has become the standard treatment for patients with resected stage II-III NSCLC. However, the five-year survival advantage of ACT is only 4%-15% suggesting that many patients do not benefit. Management of early stage lung cancer following surgical resection still relies on metrics such as tumor size and lymph node status to guide decision making regarding adjuvant chemotherapy (ACT). Given the morbidity associated with ACT, it is imperative to develop new prognostic tools to identify those patients with high probability of relapse.

SUMMARY

Biomarkers, methods, assays, and kits are provided for predicting the survival of a subject with a cancer, such as early-stage non-small cell lung cancer (NSCLC). These biomarkers, methods, assays, and kits can therefore be used to predict the benefit of adjuvant chemotherapy (ACT) for a subject based on their expected survivability. In some embodiments, the biomarkers, methods, assays, and kits also predict the efficacy of ACT in the subject. The assays and kits can contain primers, probes, or binding agents for detecting expression at least 2, 10, 20, 30, 40, 50, 60, 70, 71, 72, 73, 74, or 75 of the genes listed in Table 1.

The disclosed method can involve obtaining a biological sample from the subject; determining levels of at least 2, 10, 20, 30, 40, 50, 60, 70, 71, 72, 73, 74, or 75 genes listed in Table 1 in the biological sample. The method can further involve comparing the gene expression levels to control values to produce a gene profile. The method can then comprise calculating an E2F signature score from the gene profile. For example, in some embodiments, a high E2F signature score is an indication that the subject will benefit from ACT.

In particular, the biological sample can be RNA derived from formalin fixed paraffin embedded tissue. These slides are routinely collected for histology and can be used as source of RNA to derive an E2F signature score. The method can further involve treating the subject with ACT if they have a high E2F signature score.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
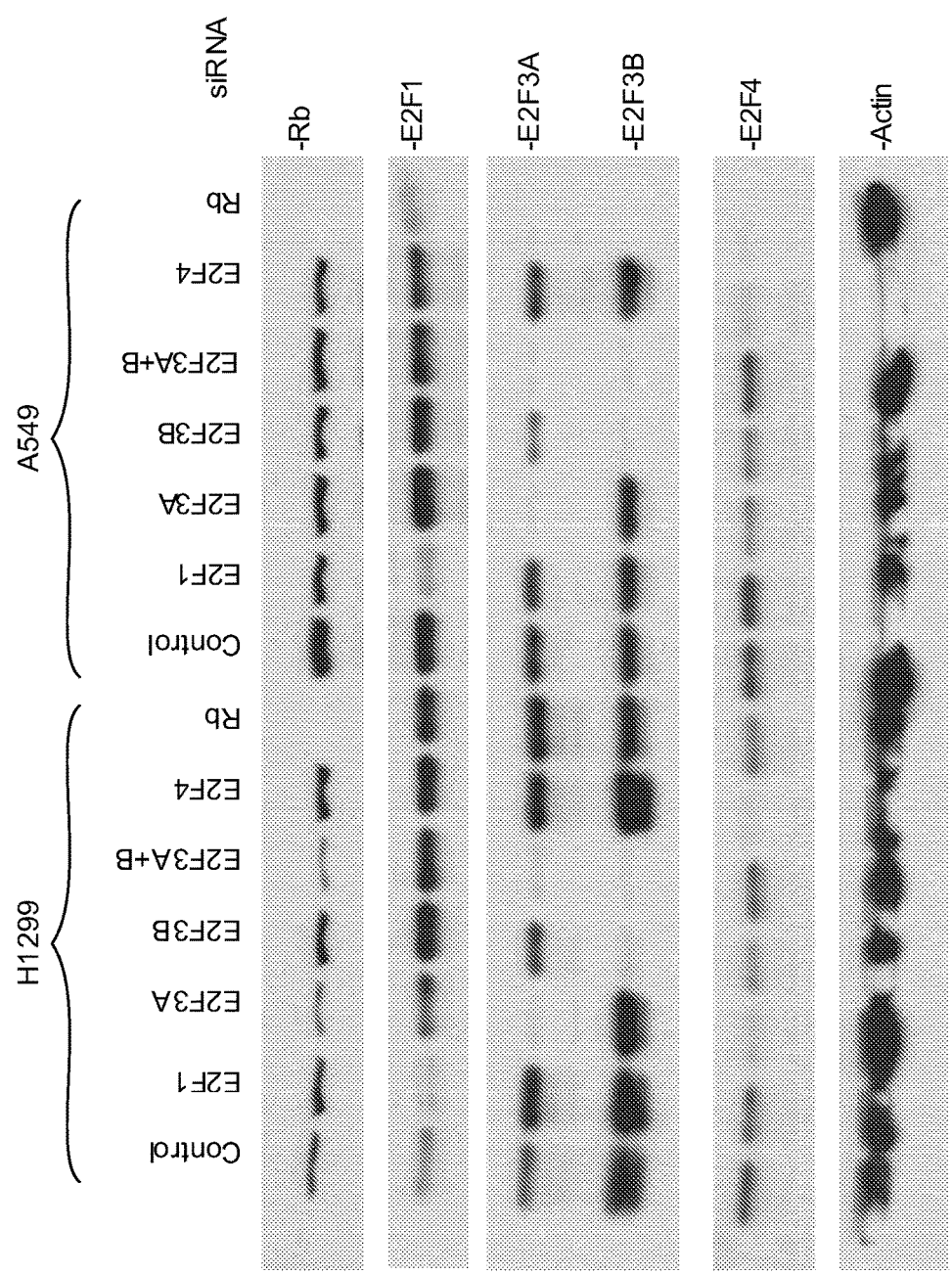
FIG. 1 is an image of a Western blot for E2F1, E2F3A, E2F3B, E2F3A+B, E2F4, Rb proteins in H1299 and A549 NSCLC lines treated with siRNAs targeting Rb, E2F1, E2F3A, E2F3B, E2F4, or Actin.

Given the morbidity associated with ACT, it is imperative to develop new prognostic tools to identify those patients with a high probability of relapse. Toward this end, small inhibitory RNAs targeting multiple E2F pathway components were used to derive an E2F gene expression signature in vitro. This signature was refined by filtering for its components that were altered in non-small cell lung cancers compared to normal tissue. Principle component analysis (PCA) was then used to identify a signature which was tested for correlation to overall survival in two large cohorts. The first of the two cohorts was the Molecular Classification of Lung Adenocarcinoma (MCLA) from the Director's Challenge Consortium and the second was a novel database on 444 lung adenocarcinomas treated as a part of Moffitt's Total Cancer Care Network.

Disclosed are methods for predicting the survival of a subject with a cancer, such as early-stage non-small cell lung cancer (NSCLC). This method can therefore be used to predict the benefit of adjuvant chemotherapy (ACT) for a subject based on their expected survivability. In some embodiments, the method also predicts the efficacy of ACT in the subject. The method generally involves first obtaining a biological sample from the subject, such as RNA derived from a tumor biopsy. Gene expression assays can then be conducted on the biological sample to determine levels of at least 2, 10, 20, 30, 40, 50, 60, 70, 71, 72, 73, 74, or 75 of the disclosed E2F signature genes. The method can further involve obtaining a dataset comprising the levels of each gene and then inputting the data into an analytical classification process that uses the data to classify the biological sample with an E2F signature score.

E2F Signature

The disclosed E2F signature is strongly prognostic. Additionally, using JBR.10 data for patients who either did or did not receive ACT allowed the determination that patients having a high E2F signature benefit from ACT (have increased overall survival), whereas patients with a low E2F signature do not. Overall, these results indicate that this approach could be optimized in the clinical setting to distinguish patients likely to benefit from ACT from those who will not.

The disclosed method involves obtaining a biological sample from the subject; determining gene expression levels of at least 2, 10, 20, 30, 40, 50, 60, 70, 71, 72, 73, 74, or 75 genes listed in Table 1 in the biological sample. Exemplary weights for calculating E2F score are provided in Table 1; however, routine multivariate analysis can be used to determine alternative weights for the genes in this list, or a subset thereof, by comparing gene expression data in patient cohorts as described herein.

TABLE 1

E2F Signature Genes and Weights

| Gene | Weight to calculate E2F score |
|---|---|
| ABAT | −0.06618 |
| ABCC6 | −0.08934 |
| ACOX2 | −0.06001 |
| AK2 | −0.04452 |
| ANXA1 | −0.03847 |
| ARHGDIB | −0.10618 |
| ARL14 | 0.013557 |
| BDH2 | −0.10153 |
| BIRC5 | 0.205929 |
| BLM | 0.1584 |
| BUB1B | 0.206879 |
| C1orf112 | 0.159249 |
| CCNE2 | 0.164075 |
| CDC6 | 0.191873 |
| CDCA4 | 0.167051 |
| CENPF | 0.184186 |
| CENPQ | 0.126635 |
| CHST11 | 0.072747 |
| CKS1B | 0.175074 |
| CPM | −0.07967 |
| CYP1B1 | −0.02709 |
| DHFR | 0.092405 |
| DOCK4 | −0.07588 |
| EVI5 | −0.03151 |
| FN1 | 0.000309 |
| GATA3 | −0.00604 |
| GBP2 | 0.011828 |
| GINS1 | 0.195944 |
| GINS2 | 0.176601 |
| GINS4 | 0.115602 |
| GLIPR1 | −0.01129 |
| HMMR | 0.181811 |
| IDS | −0.05545 |
| IMPA2 | 0.041727 |
| ISG20 | 0.02988 |
| KIAA0101 | 0.077396 |
| KIF15 | 0.200847 |
| KIF4A | 0.205465 |
| KIF5C | 0.040016 |
| LAMC2 | 0.018655 |
| LARP6 | 0.021552 |
| LAT2 | −0.05019 |
| LMNB1 | 0.160433 |
| MCM10 | 0.196864 |
| MCM2 | 0.188674 |
| MCM4 | 0.176091 |
| MDFIC | −0.03356 |
| MYB | 0.070217 |
| NFE2L3 | 0.015477 |
| NRP1 | −0.06153 |
| PLAT | −0.04571 |
| PLAUR | 0.042204 |
| PLK1 | 0.188229 |
| PLSCR4 | −0.09501 |
| PRMT3 | 0.090478 |
| PTHLH | 0.031723 |
| PTP4A1 | −0.02083 |
| QKI | −0.03663 |
| RAD51 | 0.179822 |
| RAD51AP1 | 0.193873 |
| RASGRP1 | −0.06656 |
| RRAS2 | −0.0149 |
| SEC61A2 | 0.104516 |
| SFXN1 | 0.102801 |
| SLC16A1 | 0.10311 |

TABLE 1-continued

E2F Signature Genes and Weights

| Gene | Weight to calculate E2F score |
|---|---|
| SLC1A1 | −0.05329 |
| SNAP25 | 0.0556 |
| SOX4 | 0.024096 |
| ST3GAL5 | −0.11571 |
| STIL | 0.177318 |
| SYT1 | 0.062172 |
| TGFB1I1 | −0.05406 |
| TK1 | 0.166273 |
| TMEM156 | −0.00983 |
| TMPO | 0.121226 |

The biological sample may comprise any clinically relevant tissue sample, such as a tumor biopsy. The sample may be taken from a human, or, in a veterinary context, from non-human animals such as ruminants, horses, swine or sheep, or from domestic companion animals such as felines and canines. Additionally, the samples may be from frozen or archived formalin-fixed, paraffin-embedded (FFPE) tissue samples.

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker, Lab Invest. 56:A67, (1987); and De Andres et al. Biotechniques 18:42-44, (1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MASTERPURE™ Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). Total RNA from FFPE can be isolated, for example, using High Pure FFPE RNA Microkit, Cat No. 04823125001 (Roche Applied Science, Indianapolis, Ind.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155).

Gene Expression Assays

Methods of "determining gene expression levels" include methods that quantify levels of gene transcripts as well as methods that determine whether a gene of interest is expressed at all. A measured expression level may be expressed as any quantitative value, for example, a fold-change in expression, up or down, relative to a control gene or relative to the same gene in another sample, or a log ratio of expression, or any visual representation thereof, such as, for example, a "heatmap" where a color intensity is representative of the amount of gene expression detected. Exemplary methods for detecting the level of expression of a gene include, but are not limited to, Northern blotting, dot or slot blots, reporter gene matrix, nuclease protection, RT-PCR, microarray profiling, differential display, 2D gel electrophoresis, SELDI-TOF, ICAT, enzyme assay, antibody assay, and MNAzyme-based detection methods. Optionally a gene whose level of expression is to be detected may be amplified, for example by methods that may include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

A number of suitable high throughput formats exist for evaluating expression patterns and profiles of the disclosed biomarkers. Numerous technological platforms for performing high throughput expression analysis are known. Generally, such methods involve a logical or physical array of the subject samples, the biomarkers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, Tex.), the SECTOR® Imager with MULTI-ARRAY® and MULTI-SPOT® technologies from Meso Scale Discovery (Gaithersburg, Md.), the ORCA™ system from Beckman-Coulter, Inc. (Fullerton, Calif.) and the ZYMATE™ systems from Zymark Corporation (Hopkinton, Mass.), miRCURY LNA™ microRNA Arrays (Exiqon, Woburn, Mass.).

Alternatively, a variety of solid phase arrays can favorably be employed to determine expression patterns in the context of the disclosed methods, assays and kits. Exemplary formats include membrane or filter arrays (e.g., nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library, are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In one embodiment, the array is a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Microarray expression may be detected by scanning the microarray with a variety of laser or CCD-based scanners, and extracting features with numerous software packages, for example, IMAGENE™ (Biodiscovery), Feature Extraction Software (Agilent), SCANLYZE™ (Stanford Univ., Stanford, Calif.), GENEPIX™ (Axon Instruments).

In some embodiments, the nCounter® Analysis system (Nanostring Technologies, Seattle, Wash.) is used to detect intrinsic gene expression. This system is described in International Patent Application Publication No. WO 08/124,847 and U.S. Pat. No. 8,415,102, which are each incorporated herein by reference in their entireties for the teaching of this system. The basis of the nCounter® Analysis system is the unique code is assigned to each nucleic acid target to be assayed. The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system.

Specific reporter and capture probes are synthesized for each target. Briefly, sequence-specific DNA oligonucleotide probes are attached to code-specific reporter molecules. Preferably, each sequence specific reporter probe comprises a target specific sequence capable of hybridizing to no more than one gene of Table 1 and optionally comprises at least two, at least three, or at least four label attachment regions, said attachment regions comprising one or more label monomers that emit light. Capture probes are made by ligating a second sequence-specific DNA oligonucleotide for each target to a universal oligonucleotide containing biotin. Reporter and capture probes are all pooled into a single hybridization mixture, the "probe library". Preferably, the probe library comprises a probe pair (a capture probe and reporter) for each of the genes in Table 1.

The relative abundance of each target is measured in a single multiplexed hybridization reaction. The method comprises contacting a biological sample with a probe library, the library comprising a probe pair for the genes in Table 1, such that the presence of the target in the sample creates a probe pair—target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies).

Purified reactions are deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. Data is output in simple spreadsheet format listing the number of counts per target, per sample.

This system can be used along with nanoreporters. Additional disclosure regarding nanoreporters can be found in International Publication No. WO 07/076,129 and WO 07/076,132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Calculation of E2F Signature Score

From the disclosed gene expression values, a dataset can be generated and inputted into an analytical classification process that uses the data to classify the biological sample with an E2F signature score.

The data may be obtained via any technique that results in an individual receiving data associated with a sample. For example, an individual may obtain the dataset by generating the dataset himself by methods known to those in the art. Alternatively, the dataset may be obtained by receiving a dataset or one or more data values from another individual or entity. For example, a laboratory professional may generate certain data values while another individual, such as a medical professional, may input all or part of the dataset into an analytic process to generate the result.

Prior to input into the analytical process, the data in each dataset can be collected by measuring the values for each marker, usually in duplicate or triplicate or in multiple replicates. The data may be manipulated, for example raw data may be transformed using standard curves, and the average of replicate measurements used to calculate the average and standard deviation for each patient. These values may be transformed before being used in the models.

For example, it is often useful to pre-process gene expression data, for example, by addressing missing data, translation, scaling, normalization, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data. For example, the weights provided in Table 1 can be used with the listed genes.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill").

"Translation" of the descriptor coordinate axes can be useful. Examples of such translation include normalization and mean centering. "Normalization" may be used to remove sample-to-sample variation. Some commonly used methods for calculating normalization factor include: (i) global normalization that uses all genes on the array; (ii) housekeeping genes normalization that uses constantly expressed housekeeping/invariant genes; and (iii) internal controls normalization that uses known amount of exogenous control genes added during hybridization. In some embodiments, the intrinsic genes disclosed herein can be normalized to control housekeeping genes. It will be understood by one of skill in the art that the methods disclosed herein are not bound by normalization to any particular housekeeping genes, and that any suitable housekeeping gene(s) known in the art can be used.

Many normalization approaches are possible, and they can often be applied at any of several points in the analysis. In one embodiment, data is normalized using the LOWESS method, which is a global locally weighted scatter plot smoothing normalization function. In another embodiment, data is normalized to the geometric mean of set of multiple housekeeping genes.

"Mean centering" may also be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive is skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally, and large and small values are treated with equal emphasis. This can be important for genes expressed at very low, but still detectable, levels.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

This data can then be input into the analytical process with defined parameter. The analytic classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm.

Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2 or more. In some embodiments, it is 3 or more, 4 or more, 10 or more, or between 10 and 74. Depending on the degree of certainty sought, however, the number of features used in an analytical process can be more or less, but in all cases is at least 2. In one embodiment, the number of features that may be used by an analytical process to classify a test subject is optimized to allow a classification of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. Such algorithms classify complex spectra from biological materials to distinguish subjects as normal or as possessing biomarker levels characteristic of a particular disease state. In other embodiments, a data analysis algorithm of the disclosure comprises ANOVA and nonparametric equivalents, linear discriminant analysis, logistic regression analysis, nearest neighbor classifier analysis, neural networks, principal component analysis, quadratic discriminant analysis, regression classifiers and support vector machines. While such algorithms may be used to construct an analytical process and/or increase the speed and efficiency of the application of the analytical process and to avoid investigator bias, one of ordinary skill in the art will realize that computer-based algorithms are not required to carry out the methods of the present disclosure.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

Predicting Cancer Survivability

The disclosed biomarkers, methods, assays, and kits can be used to predict the survivability of a subject with a cancer. The disclosed biomarkers, methods, assays, and kits are particularly useful to predict survivability of early stage cancers where aggressive treatments are not routinely used. For example, markers, methods, assays, and kits can be used to predict the survivability of a subject with early stage non-small cell lung cancer (NSCLC). However, other cancers may benefit from these biomarkers, methods, assays, and kits to predict the benefit of aggressive treatment. For example, the cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Adjuvant Therapy

The calculated E2F signature score can be used to predict the benefit of an adjuvant therapy for a subject based on their expected survivability. In some embodiments, the method also predicts the efficacy of adjuvant therapy in the subject. Adjuvant therapy is additional treatment given after surgery to reduce the risk that the cancer will come back. Adjuvant treatment may include chemotherapy (the use of drugs to kill cancer cells) and/or radiation therapy (the use of high energy x-rays to kill cancer cells).

As an example, the treatment for stage I, II, and IIIA NSCLC includes surgery to remove the tumor and the surrounding lung tissue and lymph nodes. The stage of NSCLC is described by a number, one through four (Roman numerals I-IV). A higher stage of cancer means that the risk that the cancer may come back is also higher. Stage I NSCLC means that the cancer has not spread to nearby lymph nodes. Stage IA means the primary tumor is relatively small. Stage IB means the primary tumor is relatively large, or is located in a place where it is more likely to spread. A stage I cancer can usually be removed by surgery. Stage II NSCLC describes a cancer that may have spread to nearby lymph nodes. Stage IIA means the primary tumor is relatively small. Stage IIB means the primary tumor is relatively large, or is located in a place where it is more likely to spread. In a stage II cancer, both the tumor and the affected lymph nodes can usually be removed by surgery. Stage III NSCLC may be difficult to remove with surgery. When the cancer has spread to lymph nodes in the center of the chest, on the same side as where the cancer started, it is known as stage IIIA. When the cancer spreads to lymph nodes on the opposite side of the chest, it is known as stage IIIB. In general, surgery is not used for any stage IIIB lung cancer. Stage IV NSCLC has spread through the bloodstream to areas of the body outside of the lung and is not treated with surgery.

The ASCO and CCO provide recommendations for adjuvant chemotherapy (ACT) treatment for stage I, II, and IIIA NSCLC. Chemotherapy after surgery to remove the lung cancer is recommended for patients with stage IIA, IIB, and IIIA NSCLC because clinical trials have shown that it may help patients live longer. However, the five-year survival advantage of ACT is only 4%-15% suggesting that many patients do not benefit. For example, chemotherapy after surgery is generally not recommended for patients with stage IA NSCLC because there is not enough evidence to show that chemotherapy helps these patients live longer, and because these patients tend to have a good chance of long-term survival with surgery alone. For the same reasons, chemotherapy for stage IB NSCLC is generally not recommended for every patient, but it may be appropriate in some situations. Moreover, the side effects of chemotherapy may include fatigue, nausea and/or vomiting, appetite loss, and irritation around the vein where the chemotherapy is injected. Other, less common side effects include anemia (a decrease in the number of red blood cells) fever with a low number of white blood cells, hair loss, constipation, peripheral neuropathy (a numbness, or tingling of the fingertips and/or toes), kidney damage, and hearing loss. Often, these side effects go away after treatment, but damage to the nerves, kidneys, or hearing may be permanent. Because some patients (1%) who develop an infection while their white blood count is low from chemotherapy have died, it is desirable to avoid the morbidity associated with ACT if the subject is not likely to benefit.

Radiation treatment after surgery is not generally recommended for patients with stage IA, IB, IIA, or IIB NSCLC because clinical trials have shown that it does not help patients live longer. Moreover, the side effects of radiation therapy may include difficulty breathing, a sore throat, difficulty eating or swallowing, and fatigue.

The disclosed E2F signature score can be used to identify whether the subject will have improve survivability if treated with ACT and may also predict benefit of radiation therapy. For example, the method can involve administering ACT and/or radiation therapy to the subject if a high E2F signature score is calculated. The method is particularly useful in early-stage cancers where adjuvant therapy is not routinely prescribed. For example, in some embodiments, the subject has been diagnosed with Stage I or Stage II NSCLC.

EXAMPLES

Example 1

E2F Signature for Adjuvant Chemotherapy Survival

Results

The E2F/Rb pathway is central to the regulation of the mammalian cell cycle, and thus, it appears a reasonable target for the development of chemotherapeutic agents (Ma, Y., et al., *Cancer Res*, 2008. 68(15):6292-9) as well as potential prognostic or predictive marker for tumor progression (Sage, J., *Nat Med*, 2007. 13(1):30-1; La Thangue, N. B., *Nat Cell Biol*, 2003. 5(7):587-9; Johnson, D. G. and J. Degregori, *Curr Mol Med*, 2006. 6(7):731-8). Unfortunately, the E2F pathway can be altered to varying degrees and by multiple molecular mechanisms, and thus, devising a straightforward clinical assay that would reflect disruption of the E2F pathway as a whole and with a "singular" measurement has been elusive. To address this weakness, an siRNA approach combined with microarray profiling was used to derive a mRNA-based gene signature that reflects deactivation of the Rb pathway.

To accomplish this goal six siRNAs were developed that could specifically and efficiently deplete lung cancer cell lines of individual E2F components. Due to their biological prominence, E2F1, E2F3 A and B, E2F3 and Rb were chosen as targets. FIG. 1 demonstrates the efficiency and specificity of these siRNAs. H1299 and A549 NSCLC lines were treated with siRNAs targeting Rb, E2F1, E2F3A, E2F3B, E2F4, or Actin and then evaluated by Western blot for E2F1, E2F3A, E2F3B, E2F3A+B, E2F4, Rb protein expression.

Next, these two cell lines were subjected to microarray profiling to detect genes whose expression levels were significantly altered by these depletion studies. These lists of genes were then filtered to identify genes that were altered in 5 of the six depletions and further filtered to identify a list of one-hundred genes. Principle component analysis was then used to represent the signature which was tested for correlation to overall survival in two large cohorts. The first of the two cohorts was the Molecular Classification of Lung Adenocarcinoma (MCLA) from the Director's Challenge Consortium and the second was a database on 444 lung adenocarcinomas treated as a part of Moffitt's Total Cancer Care Network. The E2F signature is strongly prognostic in both cohorts with P values of $3.52 \times 10^{-7}$ and $3.11 \times 10^{-7}$, respectively.

Figure 2:
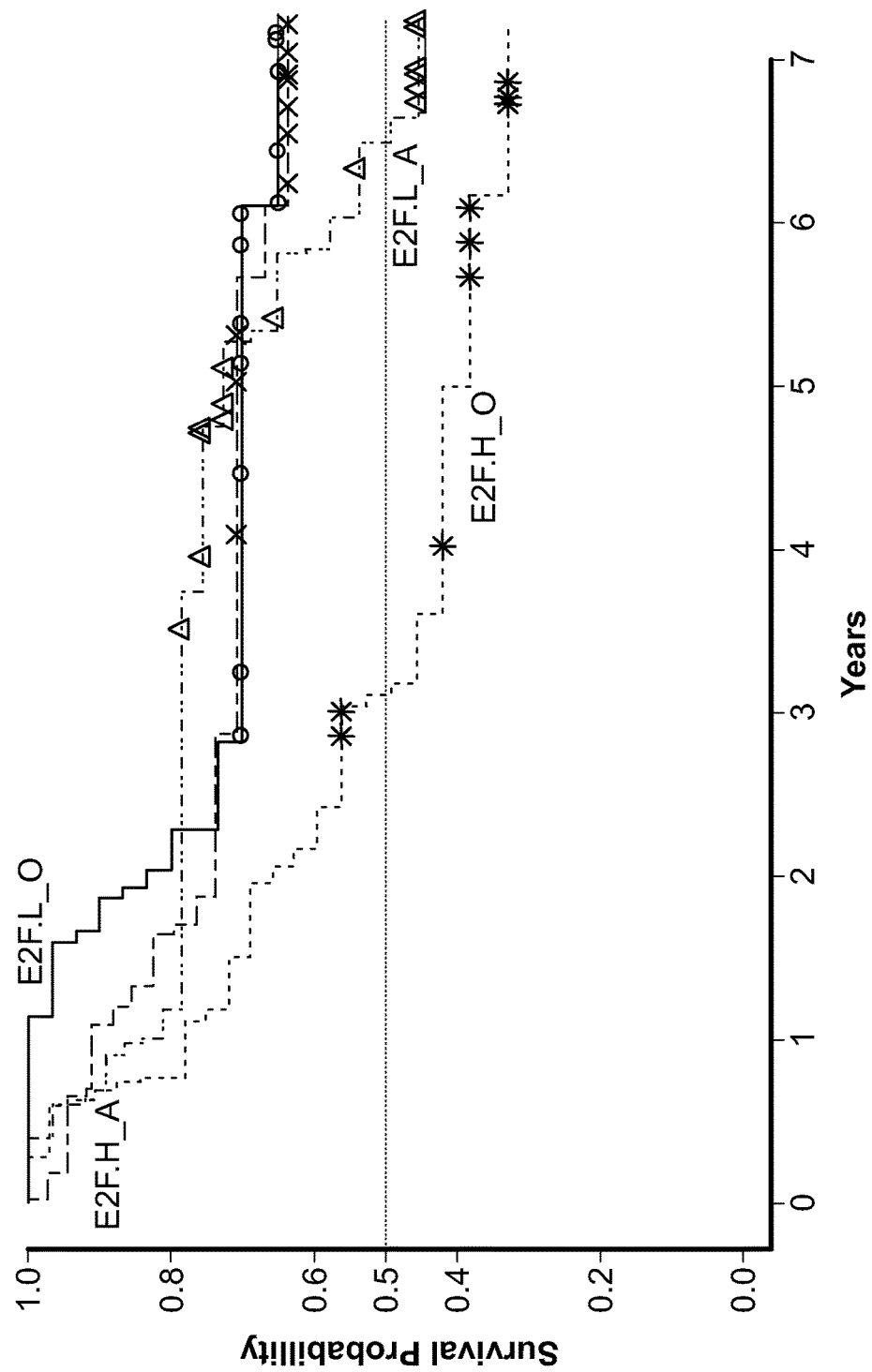
FIG. 2 is a graph showing predictive effect (survival probability as a function of time) of the E2F signature in a 133 patient cohort (JBR.10 trial): interaction effect (HR=0.29; p=0.02). MR.L: Low MR; MR.H: High MR; ACT: group with ACT; OBS: group without ACT.

Additionally, using a published dataset for patients who either did or did not receive ACT, it was possible to determine that patients having a high E2F signature benefit from ACT (have increased overall survival), whereas patients with a low E2F signature do not (FIG. 2). Overall, these results indicate that this approach could be optimized in the clinical setting to distinguish patients likely to benefit from ACT from those who will not.

Materials and Methods

Derivation of E2F Score:

An overall E2F score was generated using principal component analysis to reflect the combined effect of the E2F targeted genes. Specifically, the first principal component (a weighted average expression among the E2F genes), as it accounts for the largest variability in the data, was used to represent the overall expression level for the signature. This approach has been used to derive the malignancy-risk gene signature in lung and breast cancer study (Aberle, D. R., et al., *N Engl J Med*, 2011. 365(5):395-409).

Evaluation of Predictive Feature:

For the predictive value, treatment effect (compared to control group) was evaluated to see any association with overall survival within each signature risk group (low- and high-score). In addition, an interaction model was conducted to determine any significance of the interaction term (between the treatments and the signature). A significant interaction effect could suggest differential treatment effects between the signature risk groups. Two datasets were used for evaluation: Director's Challenge Consortium dataset and GSE 14814 dataset.

Principal component analysis was first implemented on the Director's Challenge Consortium data to obtain the E2F score which was constructed based on the loading coefficients from the first principal component. The same loading coefficients were also used to compute the E2F score for the GSE 14814 dataset. The median of the E2F score in the Director's Challenge Consortium dataset was used as the cutoff to form low and high E2F score groups in each of the both datasets to test the predictive effect.

Example 2

NanoString™ Assay to Obtain E2F Signature

A NanoString™-based practical molecular assay was developed to analyze RNA derived from formalin fixed paraffin embedded (FFPE) samples to identify those early-staged NSCLC patients who are mostly likely to benefit clinically from ACT. Thus far, Affymetrix®-based gene expression data has been used to define the E2F signature. Unfortunately, Affymetrix®-based assays require the isolation of large amounts of fresh frozen (FF) tissues which are generally not available for the majority of archived patient sample since maintaining frozen samples is very costly. In contrast, FFPE tissues are collected and stored long-term on all surgical patients and represent a vast reservoir of archival tumor specimens. Recent studies demonstrate that mRNA sufficient in quality and quantity can be retrieved from lung cancer FFPE tissues allowing robust prediction of high risk lung cancer patients after surgical resection similar to that found with fresh frozen tissue (Kratz, J. R., et al., *Lancet*, 2012. 379(9818):823-32; Xie, Y., et al., *Clin Cancer Res*, 2011 17(17):5705-14). A potential roadblock in the translation of these recent findings into clinical application is that neither used assays that can be easily adapted to clinic. To address this weakness, the NanoString nCounter™ format can be used (Geiss, G. K., et al., *Nat Biotechnol*, 2008. 26(3):317-25). The NanoString™ assay is direct (there is no amplification steps that can bias signal strength), it has few steps and no enzymatic steps that might be inhibited by contaminants (Malkov, V. A., et al., *BMC Res Notes*, 2009. 2:80). The assay allows numerous probes in a single reaction (up to 800) and it is ideal for small nucleic acid fragments such as those present in formalin-fixed paraffin embedded tissues (Reis, P. P., et al., *BMC Biotechnol*, 2011. 11:46). The NanoString™ assay has the same sensitivity as quantitative PCR methods (requiring only 100 ng of material) and demonstrates good concordance with these assays and microarray assays in direct comparisons (Reis, P. P., et al., *BMC Biotechnol*, 2011. 11:46; Northcott P. A., *Acta Neuropathol*, 2012. 123(4):615-26; Barlin J. N., *Gynecol Oncol.* 2012).

A 75-gene signature was identified that can be used to determine if patients with early-stage NSCLC are likely to benefit from adjuvant chemotherapy (ACT) using NanoString™ analysis of RNA derived from FFPE. This gene signature was derived from a comprehensive analysis of the E2F/Rb pathway in vitro using siRNA, and has been found to correlate with overall survival in two large cohorts. The first of the cohorts was the Molecular Classification of Lung Adenocarcinoma (MCLA) from the Director's Challenge Consortium ($p=3.52\times10^{-7}$) and the second was a novel database of 444 lung adenocarcinomas treated as a part of Moffitt's Total Cancer Care Program ($p=3.11\times10^{-7}$). The E2F signature is strongly prognostic in both of these cohorts. Moreover, using a 133 patient cohort from the JBR. 10 trial (Zhu et al. Journal of Clinical Oncology (2010)28:4417), it was determined that patients with a high E2F signature benefit from ACT, whereas patients with a low E2F signature do not (p=0.01). The assay can be run using RNA extracted from paraffin-embedded tissue samples and a validated NanoString® platform for simple profiling of gene expression at reduced time and material costs.

This technology is an mRNA-based gene signature that reflects deactivation of the Rb pathway and is intended to objectively help physicians predict Stage Ib-II NSCLC patient response to adjuvant chemotherapy (ACT, cisplatin/vinorelbine).

FFPE and FF tissue was obtained from a cohort of 48 patients at Moffitt. Microarray and NanoString assays were performed on the fresh frozen and NanoString on the FF and FFPE RNA. A near perfect correlation was obtained for NanoString assay of either FFPE tissue or FF tissue, and good correlations were obtained with microarray data. This also resulted in a trimming of the codesets and controls.

Table 1 includes the current genes list (75 genes). Assays can also include internal controls (e.g., C2orf42, DEDD, GIGYF2, HDAC3, PRDM4, SART3, USP4, and BIRC6) that are expressed at very consistent level in several databases to allow for normalization between samples and batches of samples using RNA extracted from paraffin-embedded tissue using a validated NanoString® platform for simple profiling of gene expression.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject with early-stage non-small cell lung cancer (NSCLC), comprising
    a) measuring gene expression levels with probes specific to a combination of 70 or more E2F regulated genes selected from the group consisting of the genes listed in Table 1 in a biological sample;
    b) comparing the gene expression levels to control values to produce a gene profile;
    c) calculating an E2F signature score from the gene profile; and
    d) treating the subject with adjuvant chemotherapy (ACT) having an E2F signature score that is higher than a determined median cutoff level.

2. The method of claim 1, wherein the biological sample is RNA obtained from formalin fixed paraffin embedded tissue.

3. The method of claim 1, wherein the subject has been diagnosed with stage I NSCLC.

4. The method of claim 1, wherein gene expression levels of the genes listed in Table 1 are determined using a nanoreporter code system.

* * * * *